US 8,058,064 B2

(12) United States Patent
Nakauchi et al.

(10) Patent No.: US 8,058,064 B2
(45) Date of Patent: Nov. 15, 2011

(54) SAC-LIKE STRUCTURE ENCLOSING HEMATOPOIETIC PROGENITOR CELLS PRODUCED FROM ES CELLS AND METHOD FOR PREPARING BLOOD CELLS

(75) Inventors: Hiromitsu Nakauchi, Tokyo (JP); Koji Eto, Tokyo (JP); Naoya Takayama, Tokyo (JP); Hidekazu Nishiki-i, Tokyo (JP); Hiroko Tsukui, Tokyo (JP)

(73) Assignee: The University of Tokyo, Tokyo (JP)

( * ) Notice: Subject to any disclaimer, the term of this patent is extended or adjusted under 35 U.S.C. 154(b) by 8 days.

(21) Appl. No.: 12/444,237

(22) PCT Filed: Oct. 4, 2004

(86) PCT No.: PCT/JP2007/001081
§ 371 (c)(1),
(2), (4) Date: Jun. 10, 2009

(87) PCT Pub. No.: WO2008/041370
PCT Pub. Date: Apr. 10, 2008

(65) Prior Publication Data
US 2010/0197016 A1    Aug. 5, 2010

(30) Foreign Application Priority Data
Oct. 4, 2006 (JP) .................................. 2006-272555

(51) Int. Cl.
*C12N 5/00* (2006.01)
(52) U.S. Cl. .......................... 435/377; 435/372; 435/373
(58) Field of Classification Search ........................ None
See application file for complete search history.

(56) References Cited

U.S. PATENT DOCUMENTS
2006/0099198 A1  5/2006  Thomson et al.

FOREIGN PATENT DOCUMENTS
| JP | 2004-350601 | 12/2004 |
| JP | 2005287479 | 10/2005 |
| JP | 2006-061106 | 3/2006 |
| JP | 2006-141356 | 6/2006 |
| WO | WO03050251 | 6/2003 |
| WO | WO2005019441 | 3/2005 |

OTHER PUBLICATIONS

Hirashima et al. Maturation of Embryonic Stem Cells into Endothelial Cells in an in Vitro Model of Vasculogenesis. Blood, 1999, vol. 93, pp. 1253-1263.*
Huyhn et al. Characterization of Hematopoietic Progenitors from Human Yolk Sacs and Embryos. Blood, 1995, vol. 86, pp. 4474-4485.*
Cheng et al. Human Mesenchymal Stem Cells Support Megakaryocyte and Pro-Platelet Formation From CD34+ Hematopoietic Progenitor Cells. J. Cellular Physiol., 2000, vol. 184, pp. 58-69.*
Eto et al., Proc. Acad. Sci. USA 2002; 99: 12819-12824.
Fujimoto et al., Blood 2003; 102: 4044-4051.
Hiroyama et al., Exp. Hematol. 2006; 34: 760-769.
Gaur et al., J Thromb Haemost. 2005; 4: 436-442.
Bergmeier, W et al., Cir Res 95: 677-683, 2004.
Gardiner, EE et al., J Thrombosis and Haemostasis, 5: 1530-1537, 2007.
Jiang et al., "High dose chemotherapy and transplantation . . . ", Journal of Chemotherapy vol. 17, pp. 302-308 (2005).
Vodyanik et al., "Human embryonic stem cell-derived CD34+ cells: efficient production in the coculture with OP9 stromal cells and analysis of lymphohematopoietic potential", 2005, 105: 617-626.
Chinese Examination Report corresponding to Application No. 200780038694.6, dated Jul. 5, 2010.
GB Examination Report corresponding to Application No. GB0906137.5, dated Aug. 4, 2010.

* cited by examiner

*Primary Examiner* — Deborah Crouch
(74) *Attorney, Agent, or Firm* — Pearne & Gordon LLP (57) ABSTRACT

An object of the present invention is to provide a sac-like structure enclosing hematopoietic progenitor cells and a method for preparing the sac-like structure as well as a method for efficiently preparing blood cells such as mature megakaryocytes and platelets from the sac-like structure. The present invention provides a sac-like structure enclosing hematopoietic progenitor cells, the sac-like structure being obtained by plating ES cells onto feeder cells and culturing the ES cells under suitable conditions for inducing hematopoietic progenitor cell differentiation. Moreover, the present invention provides a method for producing various blood cells, the method comprising further culturing hematopoietic progenitor cells enclosed in the sac-like structure under suitable conditions for inducing blood cell differentiation.

14 Claims, 13 Drawing Sheets

A   Blight Field

B   anti-human Flk-1

Fig.9 n. Neutrophil
m. Macrophage
nm. Neutrophil/Macrophage
E. Erythrocyte
Mixed. Colonies of multiple lineages

Fig.10 n. Neutrophil
m. Macrophage
nm. Neutrophil/Macrophage
E. Erythrocyte
Mixed. Colonies of multiple lineages

Integrin αIIb

DAPI

SAC-LIKE STRUCTURE ENCLOSING HEMATOPOIETIC PROGENITOR CELLS PRODUCED FROM ES CELLS AND METHOD FOR PREPARING BLOOD CELLS

TECHNICAL FIELD

The present invention relates to a sac-like structure enclosing hematopoietic progenitor cells, which is prepared from ES cells (Endothelial Sac; embryonic stem-sac; or ES-sac). Moreover, the present invention relates to a method for preparing blood cells using the aforementioned sac-like structure.

BACKGROUND ART

For the treatment of blood-related diseases including leukemia as a typical example, it is extremely important to stably amplify and supply blood cells in an amount necessary for such treatment. Thus, to date, many researchers have attempted to efficiently amplify hematopoietic stem cells or hematopoietic progenitor cells. Among blood cells, megakaryocytes are cells capable of producing proplatelets, and further, platelets. Hence, they occupy an important place in therapeutic applications. Among blood cells, platelets are cells essential for blood coagulation (hemostasis). Accordingly, the demand for platelets is extremely high in leukemia, bone marrow transplantation, anticancer therapy, etc. To date, the platelets have been supplied by a method involving collection from blood donors. However, such method involving collection from blood donors would hardly achieve stable platelet supply due to chronic shortage of donors, inability to preserve the collected platelets in a frozen state, etc. At the same time, attempts have been made to apply a method involving administration of TPO, a method of differentiating megakaryocytes from umbilical cord blood or myelocytes, etc. However, such TPO administration has not yet been put to practical use because antibodies neutralizing the TPO are produced after administration of the TPO. Also, the method of differentiating megakaryocytes from umbilical cord blood or myelocytes is not suitable as a method of stably providing platelets because it is able to obtain only small quantities of hematopoietic stem cells serving as a source of megakaryocytes.

In recent years, in vitro amplification of hematopoietic stem cells or hematopoietic progenitor cells, which are obtained only in a slight amount from living bodies, has actively been conducted. For example, there have been reports on: a method for establishing, from mouse ES cells, a hematopoietic stem cell line capable of self-renewing and differentiating even into lymphocytes (Patent Document 1); a method comprising inducing in vitro ES cells of a primate to differentiate, then transplanting in utero the obtained cells into a sheep fetus, and obtaining differentiated primate hematopoietic cells from the newborn lamb (Patent Document 2); and a method for conveniently and stably amplifying in vitro CD34-positive/CD38-negative cells that maintain undifferentiation of hematopoietic stem cells (Patent Document 3).

In order to stably supply platelets, a method for allowing hematopoietic stem cells or hematopoietic progenitor cells to efficiently differentiate into megakaryocytes and platelets. Therefore, attempts have actively been made also to induce megakaryocytes, and further, platelets, from ES cells derived from various types of animals. Eto et al. have revealed that mouse ES cells are induced to differentiate into megakaryocytes by coculturing them with OP9 stromal cells (Non-Patent Document 1). Fujimoto et al. have reported that platelet induction had been confirmed using a method similar to that of Eto et al. (Non-Patent Document 2). Moreover, there are also the following reports: a report regarding successful induction of megakaryocyte differentiation from monkey ES cells (Non-Patent Document 3); and a report regarding successful induction of megakaryocyte differentiation from human ES cells (Non-Patent Document 4). However, the release of platelets has not confirmed in any of these documents. Moreover, in order to stably obtain a therapeutically necessary amount of blood cells, other than platelets or megakaryocytes, it is necessary to efficiently obtain hematopoietic stem cells or hematopoietic progenitor cells. However, it is hard to say that such method has been established.

Patent Document 1: Japanese Patent Laid-Open No. 2006-141356

Patent Document 2: Japanese Patent Laid-Open No. 2004-350601

Patent Document 3: Japanese Patent Laid-Open No. 2006-61106

Non-Patent Document 1: Eto et al., Proc. Acad. Sci. USA 2002; 99: 12819-12824.

Non-Patent Document 2: Fujimoto et al., Blood 2003; 102: 4044-4051.

Non-Patent Document 3: Hiroyama et al., Exp. Hematol. 2006; 34: 760-769.

Non-Patent Document 4: Gaur et al., J Thromb Haemost. 2005; 4: 436-442.

DISCLOSURE OF THE INVENTION

Problems to be Solved by the Invention

Under such circumstances, the present inventors have conducted intensive studies regarding a method for efficiently obtaining hematopoietic progenitor cells and a method for obtaining megakaryocytes and platelets. As a result, the present inventors have succeeded in preparing a sac-like structure, in which hematopoietic progenitor cells are concentrated. Further, the inventors have also succeeded in preparing platelets from human ES cells for the first time, thereby completing the present invention.

Accordingly, the present invention relates to a sac-like structure enclosing hematopoietic progenitor cells and a method for preparing the sac-like structure.

Furthermore, the present invention relates to a method for efficiently preparing blood cells such as mature megakaryocytes and platelets from the sac-like structure.

Means for Solving the Problems

By conventional techniques, it was difficult to obtain hematopoietic progenitor cells at a relatively high concentration. As a result, blood cells were also obtained only in a small amount. It has been particularly difficult to induce a therapeutically necessary amount of platelets from ES cells, and even such induction could not be conducted in the case of human ES cells. To solve these problems, the present inventors have paid attention on a sac-like structure that is obtained during the process of inducing ES cells to differentiate and have performed the induction of blood cells from the sac-like structure.

Specifically, the present invention relates to the following (1) to (10):

A first aspect of the present invention is "a sac-like structure enclosing hematopoietic progenitor cells, the sac-like structure which is obtained by plating ES cells onto feeder cells and culturing the ES cells under a suitable condition for inducing differentiation of hematopoietic progenitor cells".

A second aspect of the present invention is "the sac-like structure according to (1), wherein the suitable condition for inducing hematopoietic progenitor cell differentiation is culturing the ES cells for 14 to 16 days in the presence of VEGF".

A third aspect of the present invention is "the sac-like structure according to (1) or (2), wherein the ES cells are human-derived".

A fourth aspect of the present invention is "the sac-like structure according to any of (1) to (3), wherein the feeder cells are 10T1/2 cells or OP9 cells".

A fifth aspect of the present invention is "a method for producing blood cells, the method comprising: separating hematopoietic progenitor cells from cells forming septa in the sac-like structure according to any of (1) to (4); plating the obtained hematopoietic progenitor cells onto feeder cells; and culturing the hematopoietic progenitor cells under a suitable condition for inducing blood cell differentiation".

A sixth aspect of the present invention is "the method according to (5), wherein the blood cells are megakaryocytes and platelets".

A seventh aspect of the present invention is "the method according to (6), wherein the suitable condition for inducing blood cell differentiation is culturing the hematopoietic progenitor cells for 7 to 9 days in the presence of TPO".

An eighth aspect of the present invention is "the method according to (6), wherein the suitable condition for inducing blood cell differentiation is culturing the hematopoietic progenitor cells for 7 to 9 days in the presence of TPO, SCF, and heparin".

A ninth aspect of the present invention is "a megakaryocyte and a platelet produced by the method according to any of (6) to (8)".

A tenth aspect of the present invention is "a blood product comprising, as an active ingredient, a platelet produced by the method according to any of (6) to (8)".

Effects of the Invention

A sac-like structure according to the present invention contains hematopoietic progenitor cells concentrated at a relatively high concentration and can therefore permit efficient induction of the hematopoietic progenitor cells to differentiate into various blood cells (including e.g., neutrophils, macrophages, erythrocytes, and megakaryocytes).

Moreover, using the method for producing blood cells of the present invention, desired blood cells can be obtained efficiently in vitro. Particularly, as for human platelets, in-vitro platelet production, which has never realized so far, can be efficiently performed at a relatively large volume.

Furthermore, using the method for producing platelets of the present invention, a blood product comprising a platelet as an active ingredient can be stably supplied.

BEST MODE FOR CARRYING OUT THE INVENTION

An embodiment of the present invention relates to a sac-like structure enclosing hematopoietic progenitor cells, which is obtained by plating ES cells onto feeder cells and then culturing the ES cells under a suitable condition for inducing differentiation of hematopoietic lineage cells. In the sac-like structure, hematopoietic progenitor cells are concentrated. Thus, the sac-like structure enables efficient in-vitro induction of differentiation of the hematopoietic progenitor cells into various types of blood cells. The term "ES cells" is used herein to mean embryonic stem cells, and it refers to undifferentiated cells having pluripotency and self replication ability. A source of the "ES cells" may be any animal, and most preferably, the ES cells are human-derived. Moreover, for example, a KhES cell line may be used preferably as the human-derived ES cells. Moreover, any cell that contributes to the induction of ES cells to differentiate may be used as the "feeder cells". For example, mouse embryonic fibroblasts, preferably, a 10T1/2 cell line or OP9 cells, can be used. When the "feeder cells" are used, it is preferred that their cell proliferation should be suppressed through exposure to radiation or the like.

Culture conditions for the ES cells can be selected in suitable conditions for preparing the sac-like structure. The culture conditions differ depending on the ES cells used. For example, when a KhES cell line (human ES cells) is used, a medium can be used, which comprises IMDM supplemented with FBS at a final concentration of 15%, other supplements appropriately added thereto, etc. Furthermore, when the KhES cell line is used, it is preferred that VEGF and IGF-II should be added at concentrations on the order of 0 to 100 ng/ml and 0 to 300 ng/ml, respectively, more preferably at concentrations on the order of 20 ng/ml and 200 ng/ml, respectively, for efficiently forming the sac-like structure. Alternatively, IGF-II is not necessary added. Moreover, a culture environment differs depending on the ES cells used. For the KhES cell line, the culture conditions can be used, for example, at 5% $CO_2$ and 36 to 38° C., preferably 37° C., can be used. A culture period required to form the sac-like structure differs depending on the ES cells used. For the KhES cell line, the presence of the sac-like structure can be confirmed approximately 14 to 16 days later from plating onto feeder cells.

The formed sac-like structure takes a follicular structure and has septa composed of Flk-1 (fetal liver kinase 1; one of mesodermal cell markers)-, CD31-, CD34-, or UEA-I lectin (*Ulex europaeus*. agglutinin-1)-positive cells. This sac-like structure encloses hematopoietic progenitor cells in a concentrated state. When the hematopoietic progenitor cells existing in the sac-like structure are induced to differentiate into various types of blood cells, it is necessary to separate them from the cells constituting septa, etc. Such separation is preferably performed by physical means. For example, the septal cells and the hematopoietic progenitor cells can be separated by sifting through a sterilized sieve-like tool (e.g., cell strainer).

A further embodiment of the present invention is a method for producing various types of blood cells from hematopoietic progenitor cells separated from the sac-like structure. The obtained hematopoietic progenitor cells are plated onto feeder cells and cultured under suitable conditions for inducing desired blood cell differentiation. The expression "conditions suitable for inducing differentiation of blood cells" is used herein to mean conditions involving the addition of TPO, IL-1$\alpha$, IL-3, IL-4, IL-5, IL-6, IL-9, IL-11, EPO, GM-CSF, SCF, G-CSF, Flt3 ligand, heparin, etc., depending on the types of blood cells of interest. When differentiation of megakaryocytes and platelets is induced, the hematopoietic progenitor cells can be cultured, for example, in the presence of TPO, or in the presence of SCF, heparin and TPO, for approximately 7 to 9 days. A culture environment may be a suitable environment for inducing blood cell differentiation in vitro. The culture is performed under conditions involving, for example, 5% $CO_2$ and 36 to 38° C., preferably 37° C.

According to the present invention, the blood cells are produced in vitro. Thus, when compared with a case where blood cells naturally existing in vivo are obtained, the blood cells can be obtained simply and abundantly according to the present invention. In this respect, the method of the present invention is excellent. Particularly, in-vitro production of human platelets in a confirmable amount has not been reported so far. Hence, the present invention has achieved, for the first time, in-vitro production of human platelets.

Platelets are effective for preventing or improving decrease of platelets associated with leukemia, bone marrow transplantation, and therapy using anticancer agents. Thus, it is also possible to stably supply the human platelets obtained by the present invention in the form of a product. When such blood product is prepared, taking into consideration the storage instability of platelets, etc., other ingredients used for stabilization of platelets may also be comprised in the product. Conditions for stabilizing platelets can be selected from among methods well known by those skilled in the art. More specifically, the obtained platelets (human ES cell-derived washed platelets) can be prepared into a product, for example, according to the following method:

An ACD-A solution: FFP (fresh frozen plasma; which is prepared from whole blood obtained by blood donation and contains all of those other than blood components such as albumin and coagulation factors) is prepared at a ratio of 1:10 and stored with shaking at 20 to 24° C. after exposure to 15- to 50-Gy radiation. The ACD-A solution which contains 22 g of sodium citrate/8 g of citric acid/22 g of glucose is adjusted to a total amount of 1 L with water for injection.

When this method is used, a platelet concentration is preferably on the order of, for example, $1 \times 10^9$ platelets/mL.

Moreover, the addition of GM6001 (a broad-range hydroxamic acid-based metalloprotease inhibitor) (Calbiochem, La Jolla, Calif., USA) can prevent inactivation caused by the cleavage of a platelet functional molecule GPIb-V-IX or GPVI that occurs during cryopreservation or storage at room temperature. The present inventors have confirmed that the inactivation of mouse ES cell-derived platelets can be prevented by this method. For more information on a mechanism underlying this platelet inactivation using human platelets, see the references: Bergmeier, W et al., Cir Res 95: 677-683, 2004; and Gardiner, E E et al., J Thrombosis and Haemostasis, 5: 1530-1537, 2007.

EXAMPLES

Hereinafter, the present invention will be described more specifically with reference to Example. However, the present invention is not intended to be limited to this Example by any means.

Figure 1:
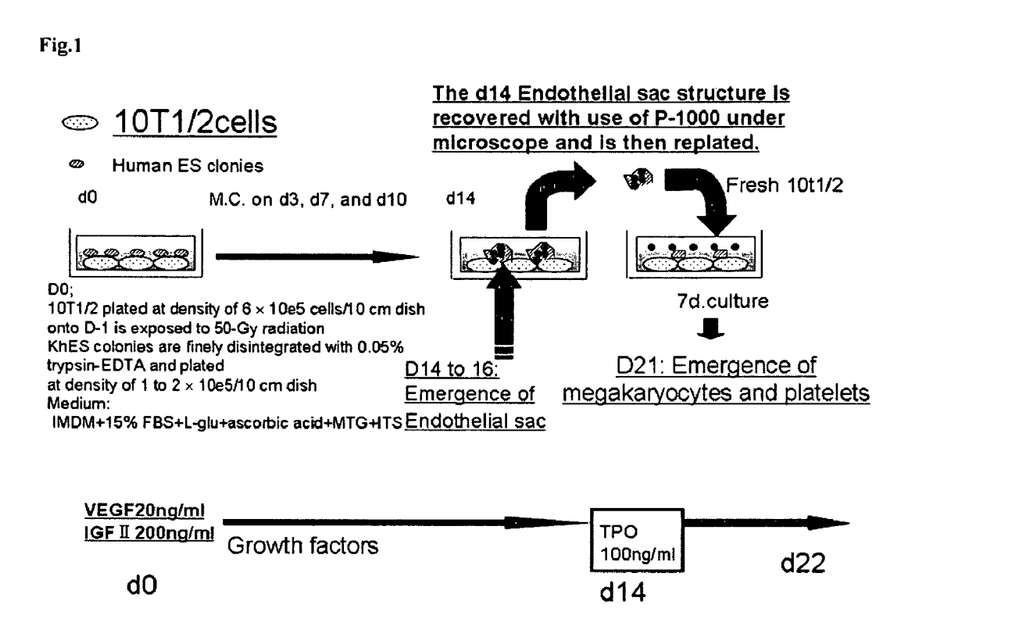
FIG. 1 is a diagram schematically showing a method for obtaining a sac-like structure.
Figure 2:
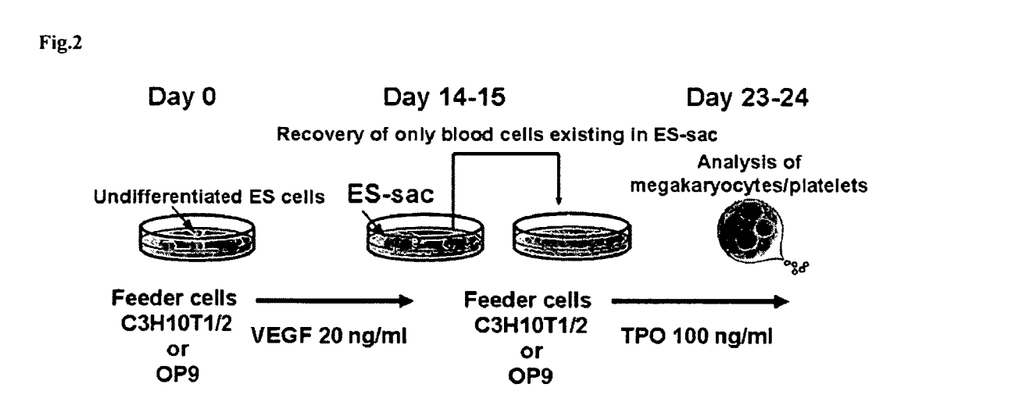
FIG. 2 is a diagram schematically showing procedures of a method for obtaining a sac-like structure and a method for preparing megakaryocytes/platelets from the sac-like structure.

The present Example relates to the induction of megakaryocyte and platelet differentiations from human ES cells (see FIGS. 1 and 2).

Preparation of Sac-Like Structure
Cell Line

KhES cell lines (KhES-1; passage 30 to 50, KhES-2; passage 20 to 40, and KhES-3; passage 20 to 40) used in the present Example were provided by Prof Norio Nakatsuji (the director of the Institute for Frontier Medical Sciences, Kyoto University) by the deliberation and consent of the Research Committee on Specified Embryos and Human ES Cells or the like, the Ministry of Education, Culture, Sports, Science and Technology, Japan. Moreover, feeder cells used were mouse embryo-derived cells, a C3H10T1/2 cell line provided by BioResource center, Riken Tsukuba Institute or OP9 cell line provided by Prof Tom Nakano (Graduate School of Medicine, Faculty of Medicine, Osaka University). On the day before the differentiation experiment, the 10T1/2 cells were plated at a density of $6 \times 10^5$ cells/10 cm dish onto a dish coated with 0.1% gelatin. On the day of the differentiation experiment, the 10T1/2 cells were exposed to 50-Gy radiation for terminating proliferation and used as feeder cells. Alternatively, when the OP9 cell line was used as feeder cells, the cells were exposed to 50-Gy radiation on the day of the differentiation experiment and used after replating.

Method for Preparing Sac-Like Structure

The KhES cells (human ES cells) were dissociated with 0.05% trypsin-EDTA (Sigma) and disrupted by use of a P-1000 pipette into small colonies, which were then plated onto the 10T1/2 cells. The composition of a medium for preparing a sac-like structure is shown in Table 1.

TABLE 1

| IMDM (Sigma) | 85% |
| FBS | 15% |
| L-Glutamine (Invitrogen) | 2 mM |
| ITS supplement (Sigma) | |
| Insulin | 10 g/ml |
| Transferrin | 5.5 mg/ml |
| Sodium selenite | 5 ng/ml |
| Ascorbic acid (Sigma) | 50 g/ml |
| MTG (Sigma) | 0.45 mM |
| Recombinant human VEGF (R&D systems) | 20 ng/ml |
| Recombinant human IGF-II (Peprotech) | 200 ng/ml |

On days 3, 7, 10, and 13 from the day of the human ES cell plating, only culture solution replacement was performed without plating cells. On days 7, 10, and 14, cells floating in the medium were used to attempt megakaryocyte/platelet induction. However, in either timing, only a very small amount of megakaryocytes was induced, and no platelet could be confirmed.

Confirmation of Sac-Like Structure

Figure 3:
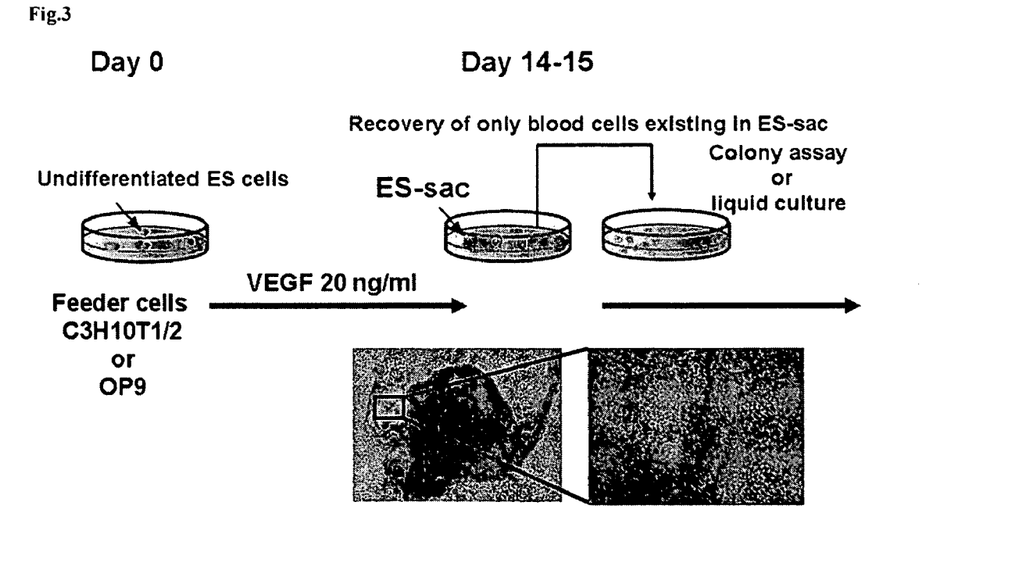
FIG. 3 is a diagram showing the process of producing a sac-like structure from undifferentiated ES cells and shows a phase-contrast microscopic observation image of the sac-like structure.
Figure 4:
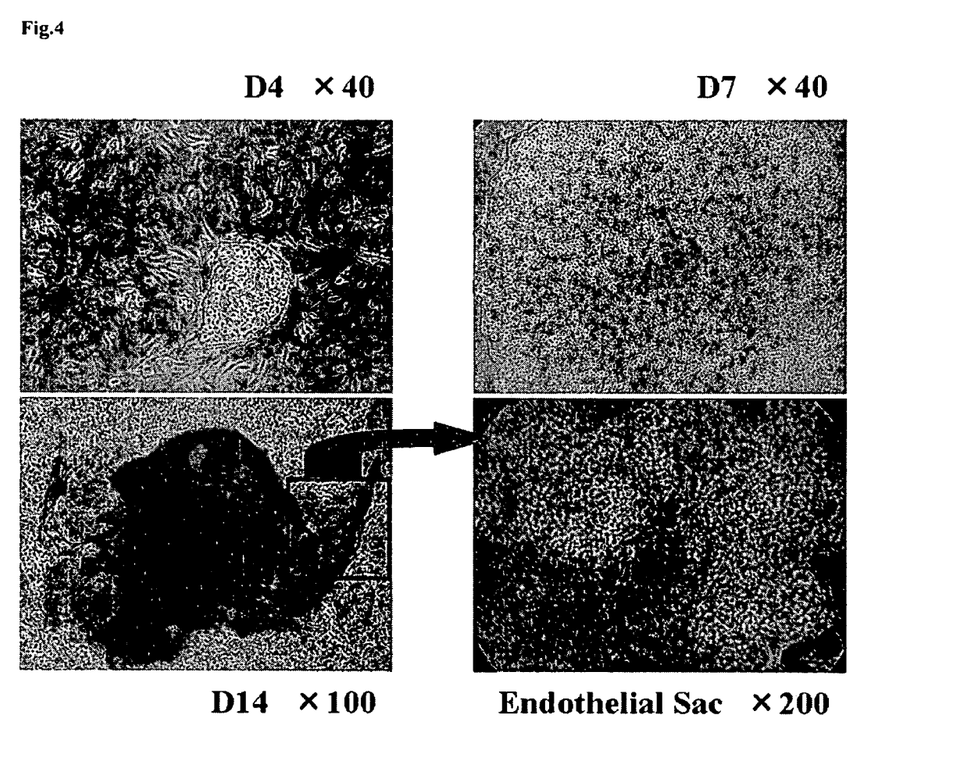
FIG. 4 is a phase-contrast microscopic observation image of a sac-like structure. D4 and D7 represent day 4 and day 7, respectively, of culture. Moreover, Endothelial Sac (embryonic stem-sac; or ES-sac) represents the sac-like structure.
Figure 5:
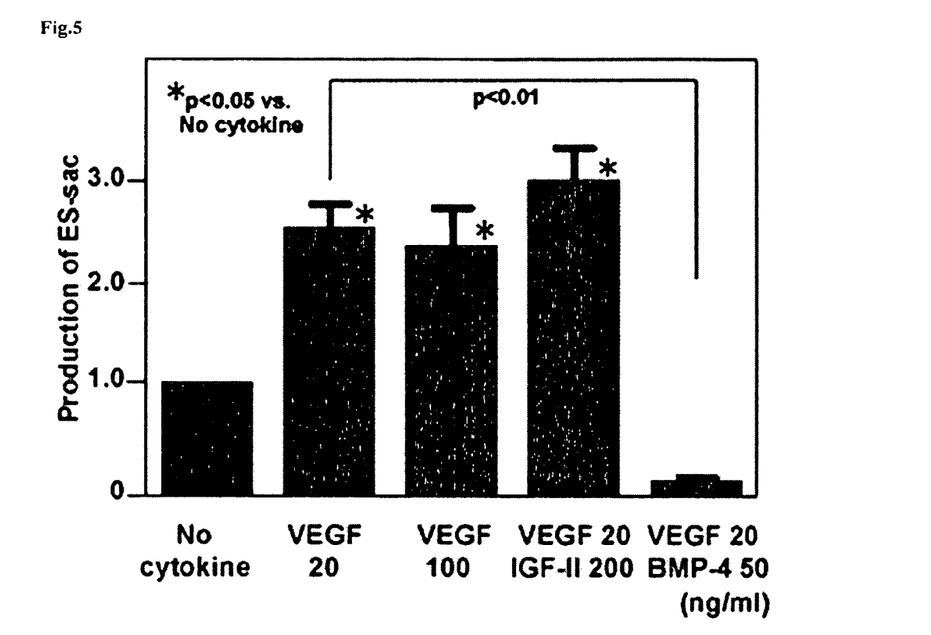
FIG. 5 shows the sac-like structure-inducing effect of VEGF. No cytokine: a control unsupplemented with cytokines such as VEGF, IGF-II, and BMP-4.
Figure 6:
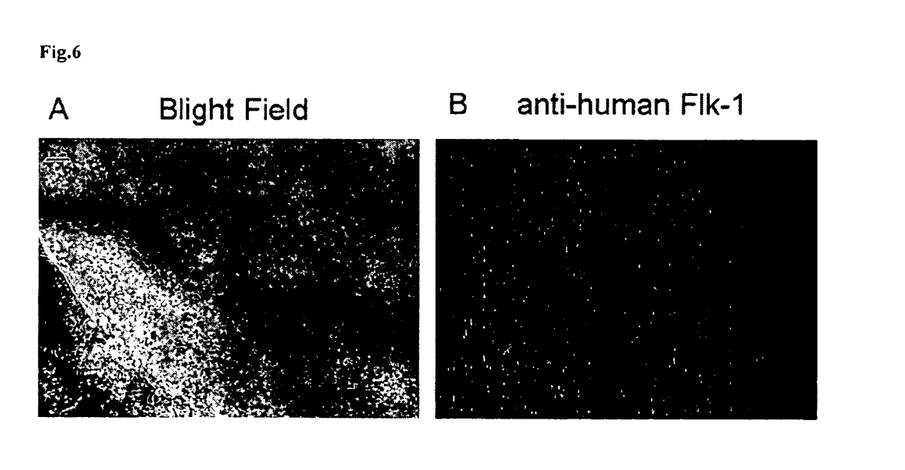
FIG. 6 shows results of fluorescent immunostaining of a sac-like structure (day 14 of culture) with anti-human Flk-1 (VEGF-R) antibodies.
Figure 7:
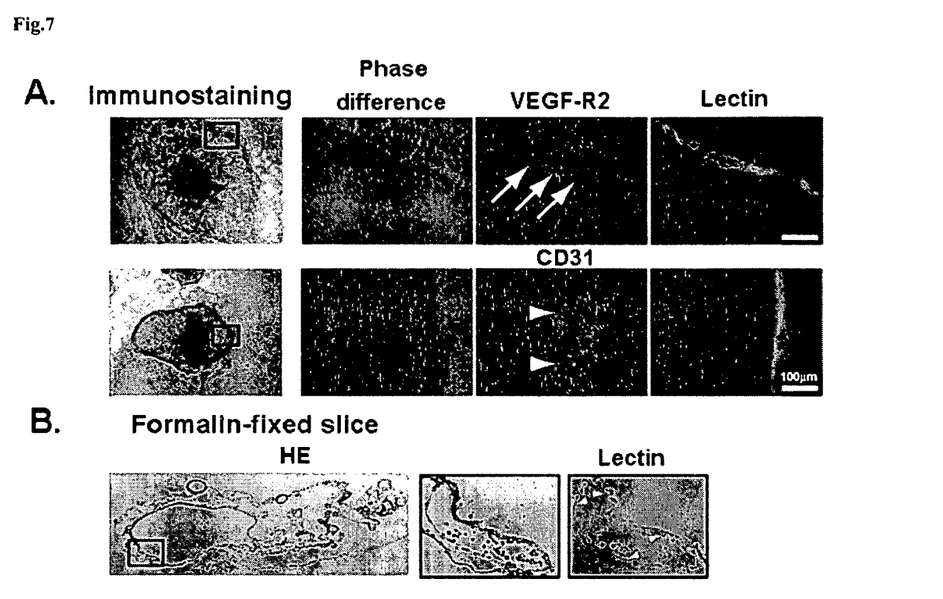
FIG. 7 shows results of fluorescent staining of a sac-like structure (day 14 of culture) with anti-human Flk-1 (VEGF-R) antibodies, anti-CD31 antibodies, or anti-UEA-I lectin antibodies. HE: hematoxylin-eosin staining The sac-like structure expressed endothelial cell markers. The inside thereof comprises a large number of vesicles compartmentalized by septa composed of lectin-positive cells. Moreover, the vesicles contain blood cell-like cells.

VEGF was added to undifferentiated ES cells. As a result, a large number of sac-like structures enclosing blood cell-like cells were confirmed around days 14 to 15 of culture (FIGS. 3 and 4). Moreover, further potentiation of sac-like structure production by IGF-II was not observed, and BMP-4 addition which reportedly has the effect of promoting hematopoietic differentiation of human ES cells inhibited the effects of VEGF (FIG. 5). This sac-like structure was collected, then methanol- or paraformaldehyde-fixed, and fluorescently stained in whole mount with anti-human Flk-1 (VEGF-R) antibodies. As a result, it was demonstrated that the inside structure of the sac takes a follicular structure compartmentalized by septa composed of Flk-1-positive cells (FIG. 6). Furthermore, this sac-like structure was fluorescently stained with anti-human Flk-1 (VEGF-R) antibodies, anti-CD31 antibodies, or anti-UEA-I lectin antibodies. As a result, it was revealed that blood cells within the sac structure can be stained with even antibodies against CD31 which is expressed in vascular endothelial cells, hematopoietic stem cells, progenitor cells, and differentiated blood cells (FIG. 7). The sac-like structure could be confirmed from all the KhES-1, KhES-2, and KhES-3 cell lines.

Characteristics of Blood Cells within Sac

Figure 8:
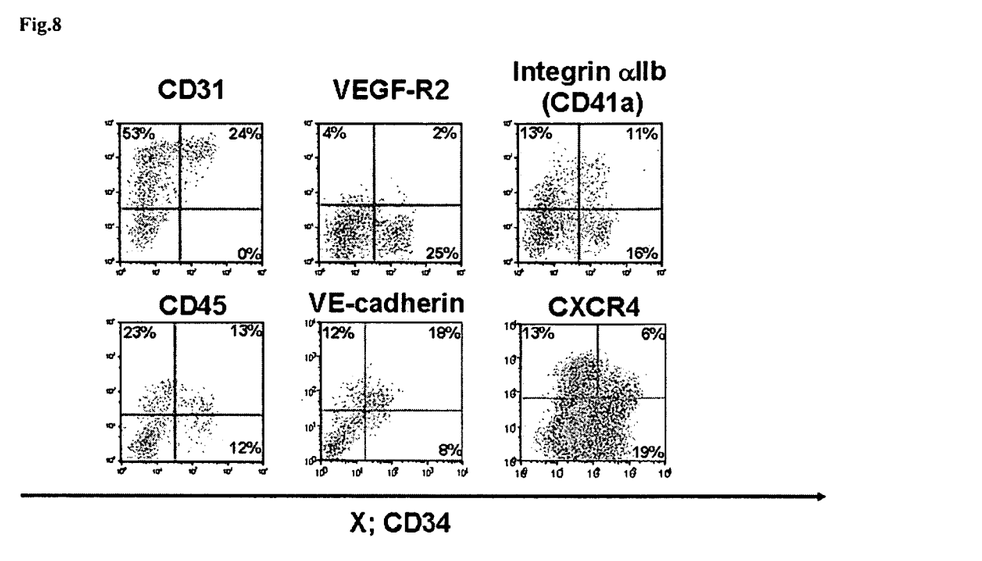
FIG. 8 shows surface antigens on blood cell progenitors within a sac-like structure (day 14 of culture) and shows results of examining the surface antigens on the blood cell progenitors within the sac-like structure using anti-human Flk-1 (VEGF-R) antibodies, anti-human CD31 antibodies, anti-human CD34 antibodies, anti-human CD41 antibodies, anti-human vascular endothelial cadherin (VE-cadherin) antibodies, or anti-human CXCR4 (stromal-derived factor-1 receptor) antibodies.

On the surface of blood cell progenitors within this sac-like structure, cell surface antigens characteristic of immature blood cells were expressed, which were stained with anti-human Flk-1 (VEGF-R) antibodies, anti-human CD31 antibodies, anti-human CD34 antibodies, anti-human CD41 antibodies, anti-human vascular endothelial cadherin (VE-cadherin) antibodies, or anti-human CXCR4 (stromal-derived factor-1 receptor) antibodies (FIG. 8). In this context, these markers can be utilized as markers in cell isolation/selection using a flow cytometer or magnetic cell separation for shortened processing time in a large-scale culture system.

Figure 9:
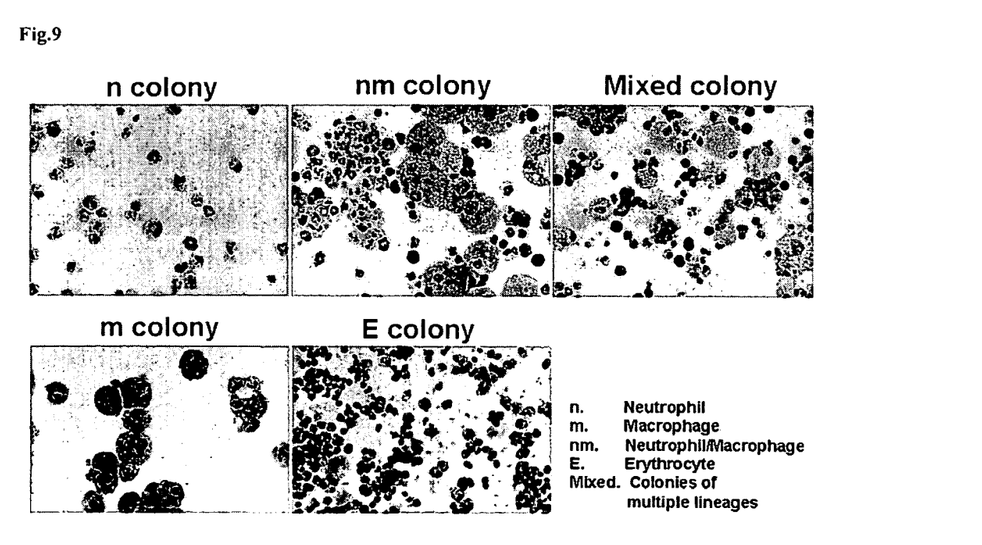
FIG. 9 shows images of various colonies on day 7 from the preparation and culture of colonies for blood cell differentiation using blood cell progenitors within a sac-like structure. The colony images are obtained as a result of wright-giemsa staining subcellular components after colony collection. The blood cell progenitors were observed to differentiate into various blood cells including a mixed colony.
Figure 10:
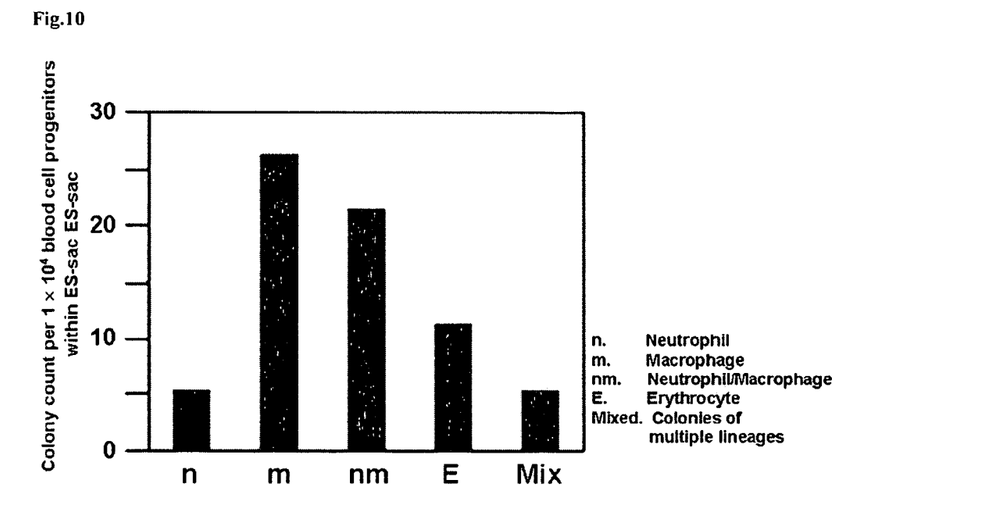
FIG. 10 shows results of quantifying colony numbers derived from various blood cells produced from $1 \times 10^4$ blood cell progenitors within a sac-like structure.

Moreover, it was demonstrated that the blood cells within the sac form, per $1 \times 10^4$ cells, approximately 100 to 200 colonies (FIG. 10) including every differentiated blood cell (except for lymphocytes) of myeloid lineage (FIG. 9).

Megakaryocyte/Platelet Induction
Megakaryocyte Induction

The sac-like structures were picked up by use of a P-1000 pipette under phase-contrast microscope and separated from the blood cells by use of a 70-μm cell strainer. The blood cells were plated at a density of 2 to $3 \times 10^4$ cells/well onto radiation-exposed 10T1/2 cells ($6 \times 10^5$ cells/6-well plate) freshly prepared in a 6-well plate. The composition of a medium for inducing megakaryocytes/platelets is shown in Table 2.

TABLE 2

| | |
|---|---|
| IMDM (Sigma) | 85% |
| FBS | 15% |
| L-Glutamine (Invitrogen) | 2 mM |
| ITS supplement (Sigma) | |
| Insulin | 10 g/ml |
| Transferrin | 5.5 mg/ml |
| Sodium selenite | 5 ng/ml |
| Ascorbic acid (Sigma) | 50 g/ml |
| MTG (Sigma) | 0.45 mM |
| Recombinant human TPO (Kirin Brewery co., Ltd.) | 100 ng/ml |

Moreover, the addition of 50 ng/ml SCF and 25 U/ml heparin to the composition shown in Table 2 doubled the amount of platelets produced.

Figure 11:
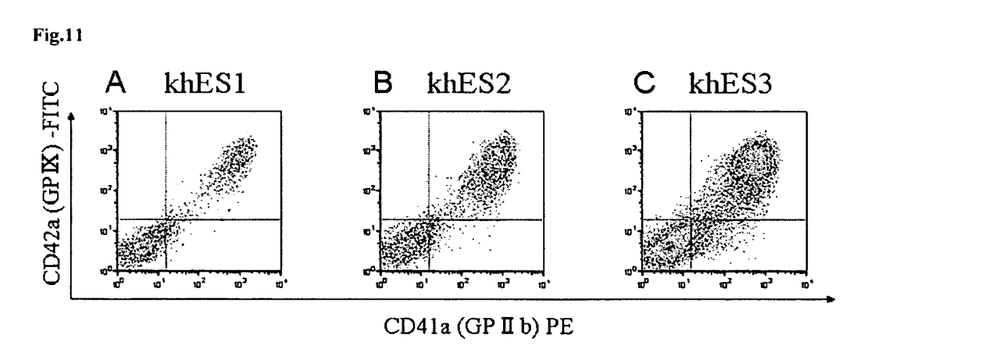
FIG. 11 shows FACS analysis of KhES cell (KhES-3 cell)-induced megakaryocytes.
Figure 12:
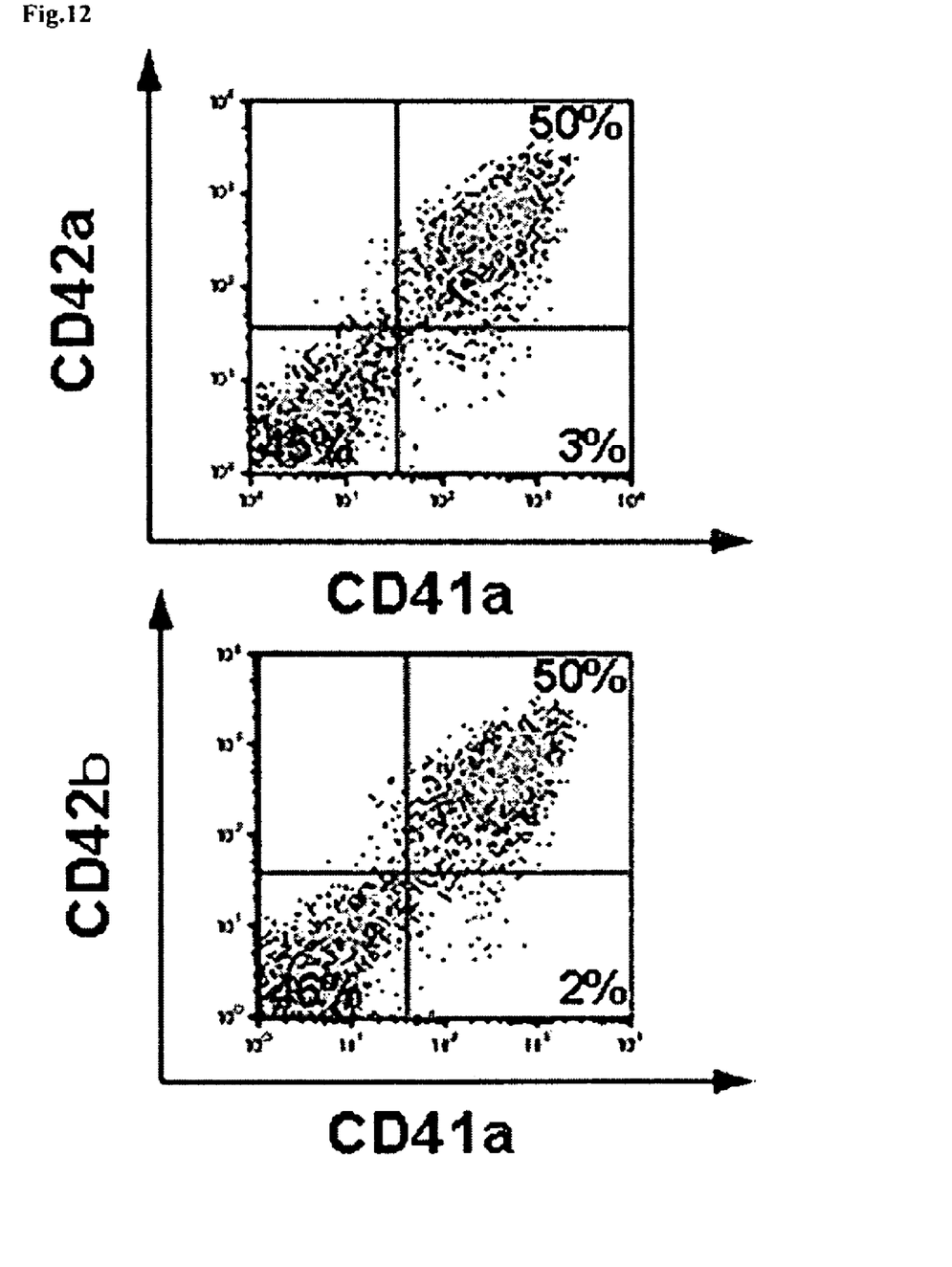
FIG. 12 shows flow cytometer analysis results of KhES cell (KhES-3 cell)-induced megakaryocytes on day 24 of culture.
Figure 13:
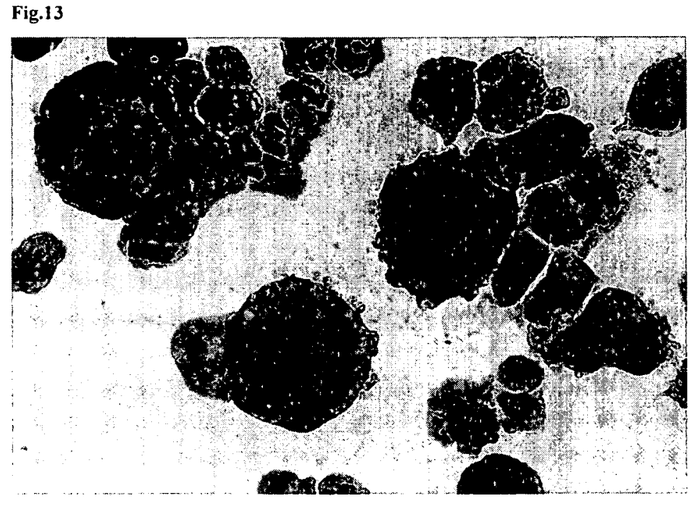
FIG. 13 is an observation image of KhES-3 cell-induced megakaryocytes on day 24 of culture that were cytospun and then wright-giemsa stained. ×40 magnification.
Figure 14:
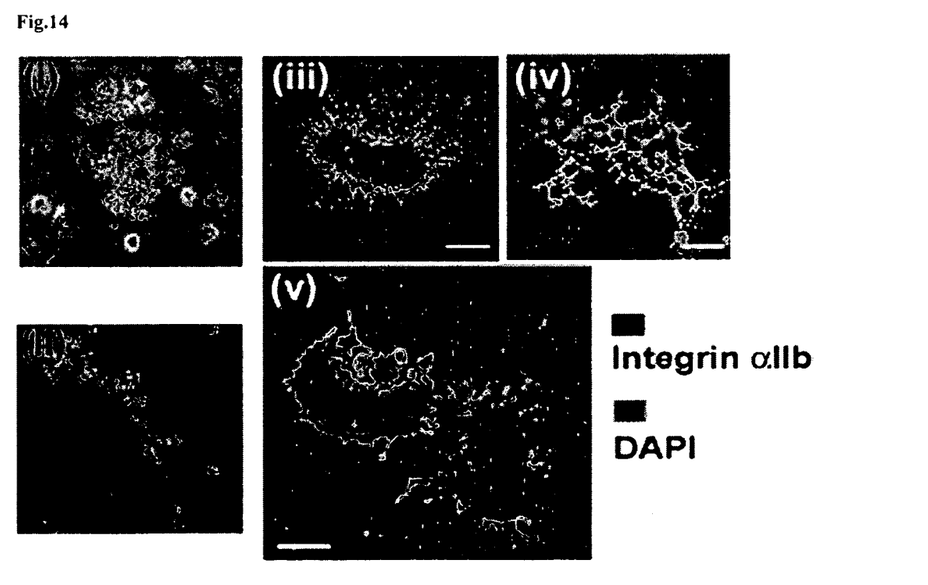
FIG. 14 shows microscopic observation images of KhES-3 cell-induced megakaryocytes and proplatelets. (i) and (ii): phase-contrast microscopic observation images of proplatelet derived from megakaryocytes induced by KhEs-3 cell. (iii), (iv), and (v): fluorescence microscopic observation images of proplatelets stained with anti-human CD41a (GPIIb; or integrin αIIb) antibodies.

After medium replacement by a culture solution with the composition shown in Table 2, the cells were cultured for additional 7 to 8 days (on days 17 and 19, the culture solution was replaced) (cumulative culture period: 21 to 22 days). As a result, approximately 50 to 60% cells positive to megakaryocyte/platelet-specific markers, CD41a (integrin αIIb chain; or GPIIb molecule) and CD42a (GPIX molecule), were detected by FACS (FIG. 11). Furthermore, in the experiment for a cumulative culture period of 22 to 24 days, approximately 50 to 60% cells positive to megakaryocyte/platelet-specific markers, CD41a (integrin αIIb chain; or GPIIb molecule), CD42a (GPIX molecule), and CD42b (GPIbα), were obtained (FIG. 12). Both CD42a (GPIX molecule) and CD42b (GPIbα) are molecules specifically expressed in mature megakaryocytes (FIG. 12). Morphologically, the obtained cells were large, polykaryotic and were consistent with the morphology of megakaryocytes (FIG. 13). From immunostaining, it was confirmed that the CD41a-positive cells are in the form of proplatelet which is allegedly involved in platelet release (FIG. 14). Moreover, RT-PCR results (semiquantitation of messenger RNA) of RNA derived from the blood cells within the sac confirmed the presence of more undifferentiated CD34+/CD41a− and more differentiated CD41a+ fractions. Thus, it was revealed that gene expression similar to that seen in normal differentiated megakaryocytes takes place in the CD41a-positive fraction.

These results proved that the blood cells within the sac are hematopoietic progenitor cells capable of efficiently producing megakaryocytes.

Confirmation of Platelets

Figure 15:
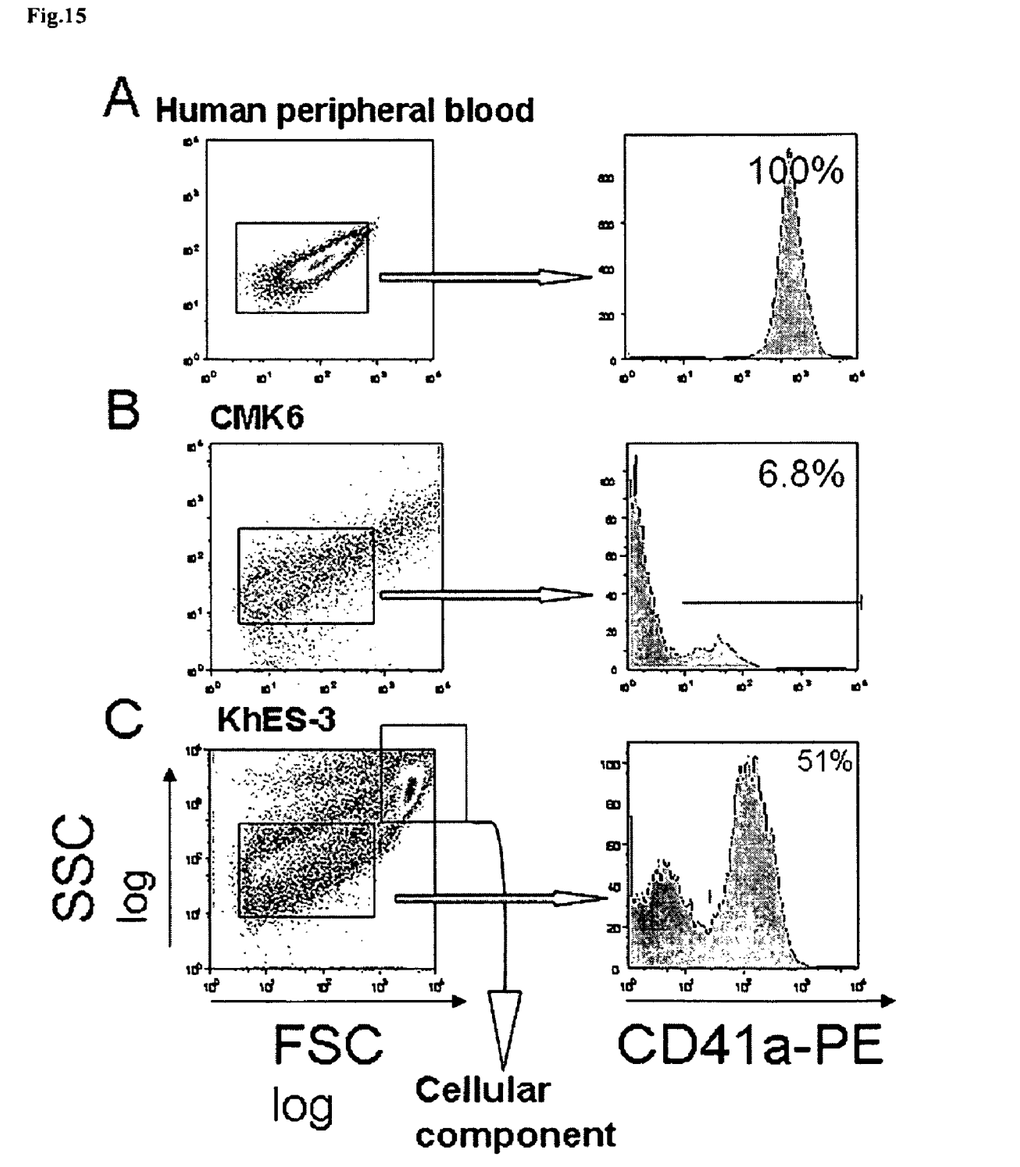
FIG. 15 shows FACS analysis results of KhES-3 cell-induced platelets. A: results of analyzing control platelets collected from human peripheral blood. B: results of analyzing KhES cell-derived platelets.

A culture supernatant on day 22 of culture was collected, and after separation of blood cells, platelets were concentrated. Platelets in human peripheral blood were collected as control platelets to set up a gate for platelet fractionation (left columns in FIG. 15). The platelets from the culture supernatant were stained with anti-CD41a-PE antibodies and analyzed with the gate by applying the same fractionation thereto. As a result, CD41a-positive particles were confirmed (right columns in FIG. 15). The culture supernatant was collected in chronological order, and the number of platelets was counted using beads. As a result, platelet production reached a peak on days 7 to 9 of culture and gradually decreased thereafter. In the present Example, 3 to $12 \times 10^4$ CD41a-positive particles were produced from 1 to $2 \times 10^5$ KhES cells.

Figure 16:
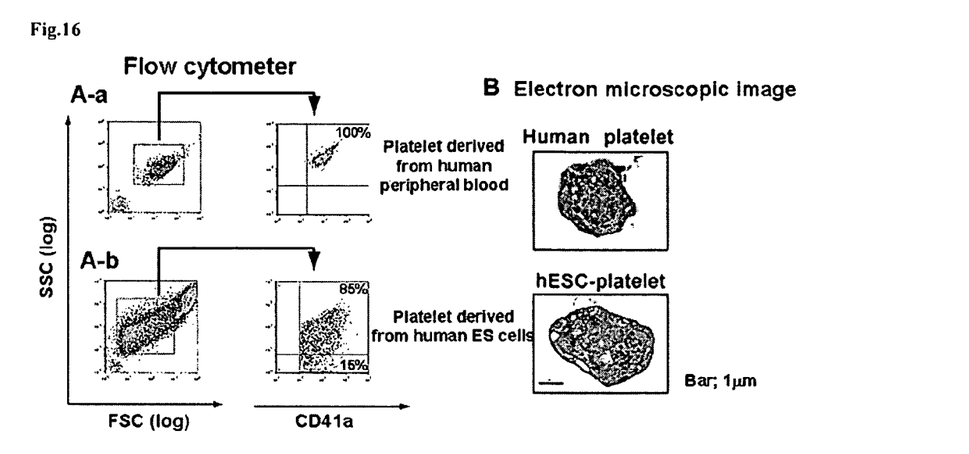
FIG. 16 shows FACS flow cytometer analysis results of KhES-3 cell-induced platelets. A-a: results of analyzing control platelets collected from human peripheral blood. BA-b: results of analyzing KhES cell-derived platelets. Both CD42a (GPIX) and CD42b (GPIbα) are molecules specifically expressed in mature megakaryocytes and platelets. B: electron microscopic photographs of human peripheral blood platelets and KhES cell-derived platelets.

Likewise, particles positive to a platelet marker CD41a were confirmed in platelets collected from a culture supernatant on day 24 of culture (FIG. 16A). In the CD41a-positive particles, GPIb and GPIX expressions of a GPIb/V/IX complex which plays an important role in thrombus formation were confirmed at efficiency of 70 to 80%. These particles were observed under electron microscopy. As a result, platelet granules and microtubular structures, etc., were confirmed, as with peripheral blood platelets (FIG. 16B).

On day 24 of culture, $5 \times 10^6$ platelets were confirmed from $1 \times 10^5$ human ES cells under conditions involving 50 ng/ml SCF (stem cell factor), 100 ng/ml TPO, and 25 U/ml heparin.

Platelet Functional Analysis 1; Fibrinogen Binding Assay

Figure 17:
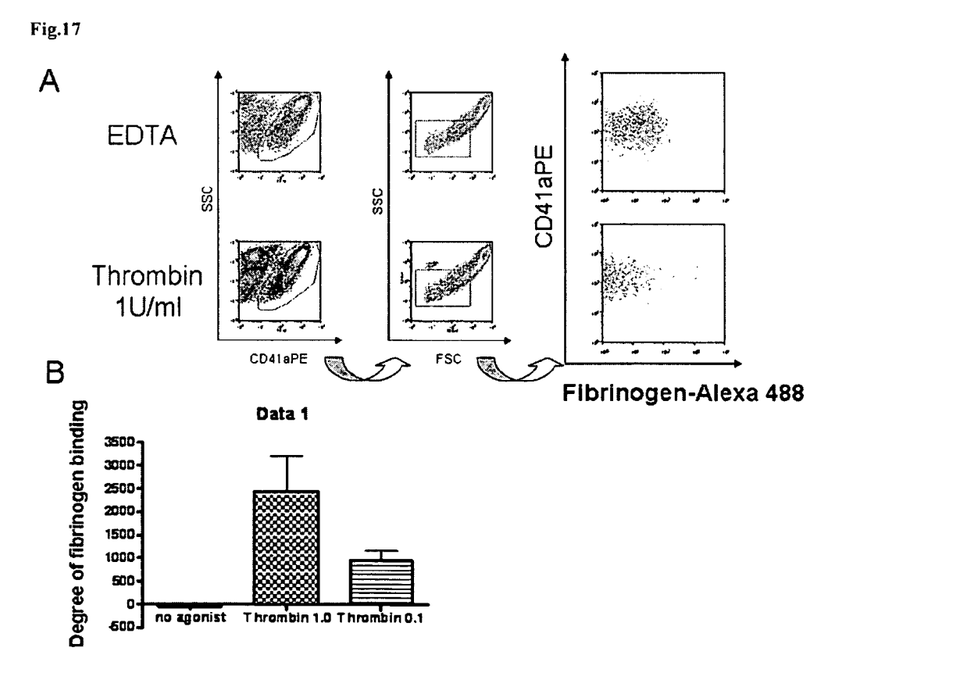
FIG. 17 shows fibrinogen binding assay results of platelets derived from KhES-3 cells. A: results obtained by procedures wherein a supernatant on day 24 of culture was collected, and after removal of subcellular components, platelets were concentrated, then stimulated with a platelet activator (thrombin), and analyzed for the degree of FITC-labeled fibrinogen binding using a flow cytometer. Results shown in the graph B show that the Alexa Fluor 488-labeled fibrinogen was bound to CD41-positive particles in a thrombin dose-dependent manner. no agonist: results obtained without Alexa Fluor 488-labeled fibrinogen.

In-vivo platelets aggregate, upon activation, through the sustained binding of a cell adhesion molecule GPIIbIIIa (integrin αIIbβ3) with fibrinogen and contribute to thrombus formation. Platelets in a supernatant on days 21 to 23 of culture were collected and reacted with Alexa Fluor 488-labeled fibrinogen in the presence of a platelet activator thrombin. As a result, CD41-positive particles that aggregated in different fractions in FSC/SSC appeared by strong aggregation attributed to the thrombin stimulation (FIG. 17A). Moreover, when the binding of fibrinogen-Alexa was observed in fractions having no strong aggregation, the binding of fibrinogen to the CD41 particles was confirmed in a thrombin dose-dependent manner (FIG. 17B).

These results proved GPIIbIIIa (integrin αIIbβ3) activation, one of platelet functions, attributed to drug stimulation and subsequent binding reaction with fibrinogen.

Figure 18:
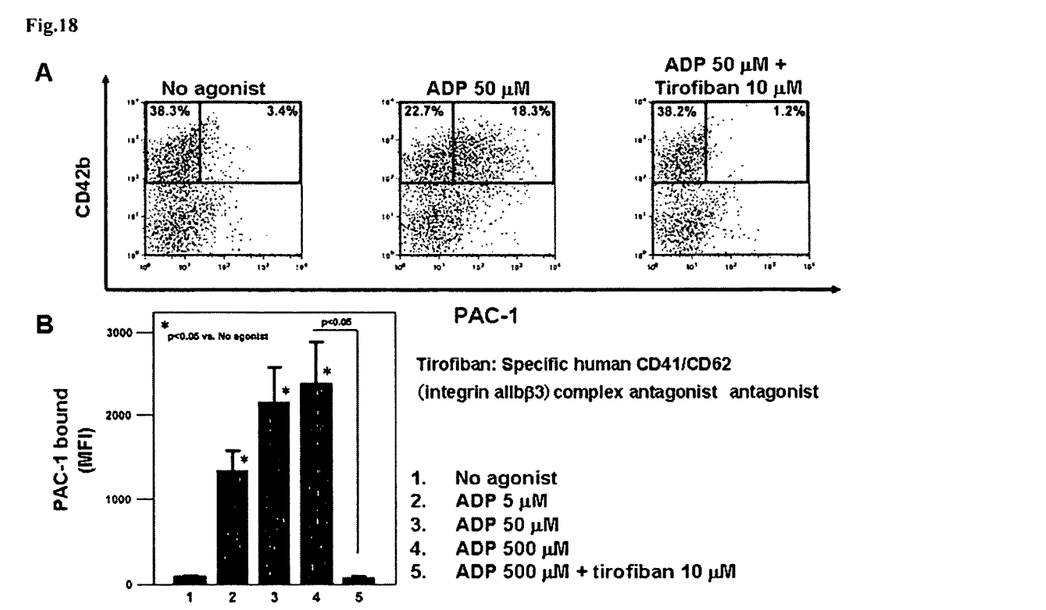
FIG. 18 shows fibrinogen binding assay results of platelets derived from KhES-3 cells. A: results obtained by procedures wherein a supernatant on day 24 of culture was collected, and after removal of subcellular components, platelets were concentrated, then stimulated with a platelet activator (ADP), and analyzed for the degree of FITC-labeled PAC-1 antibody fibrinogen binding using a flow cytometer. The PAC-1 (BD Invitrogen) is an antibody that binds only to human CD41a/CD62 (GPIIbIIIa; or integrin $\alpha$IIb$\beta$3) on the membranes of activated platelets. Results shown in the graph B show that the FITC-labeled PAC-1 antibodies were bound to CD41-positive particles in an ADP dose-dependent manner no agonist: results obtained without ADP.

Furthermore, platelets in a supernatant on days 23 to 24 of culture were collected and analyzed for integrin activation (one of platelet functions essential for hemostatic plug) using active integrin αIIbβ3-binding antibodies (trade name: PAC-1) (BD Invitrogen) labeled with FITC. As a result, integrin activation was confirmed in a concentration-dependent manner from low to high concentrations (0.5 to 500 μM) of an in-vivo platelet activator ADP (the platelets from the supernatant exhibited reactivity equivalent to that of human platelets) (FIG. 18A). Moreover, the active integrin αIIbβ3-binding antibodies (PAC-1) labeled with FITC was bound to CD41-positive particles in a thrombin dose-dependent manner, and this binding was completely inhibited by a human-specific anti-CD41a/CD62 drug tirofiban (FIG. 18B).

Platelet Functional Analysis 2: Spreading on Fibrinogen-Immobilized Solid Phase

Figure 19:
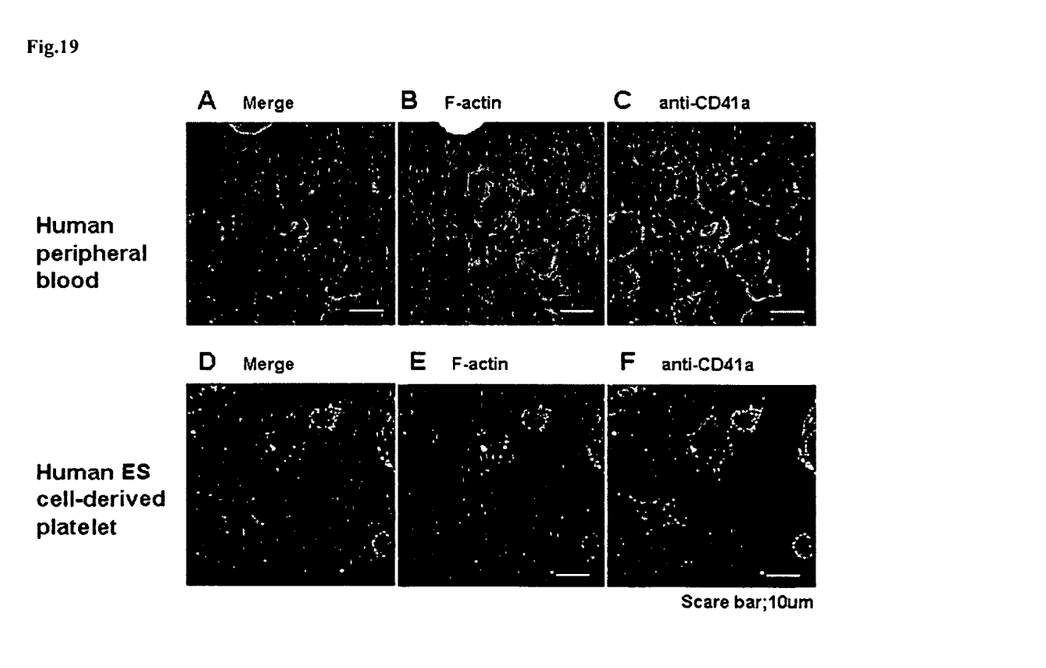
FIG. 19 shows fluorescence microscopic observation results of cytoskeletal changes exhibited by KhES-3 cell-derived platelets through PMA stimulation, as with peripheral blood-derived platelets. B and E: images of staining with anti-F-actin antibodies. C and F: images of staining with anti-CD41a antibodies. A and D: observation images obtained by merging the image B with the image C and the image E with the image F, respectively.
Figure 20:
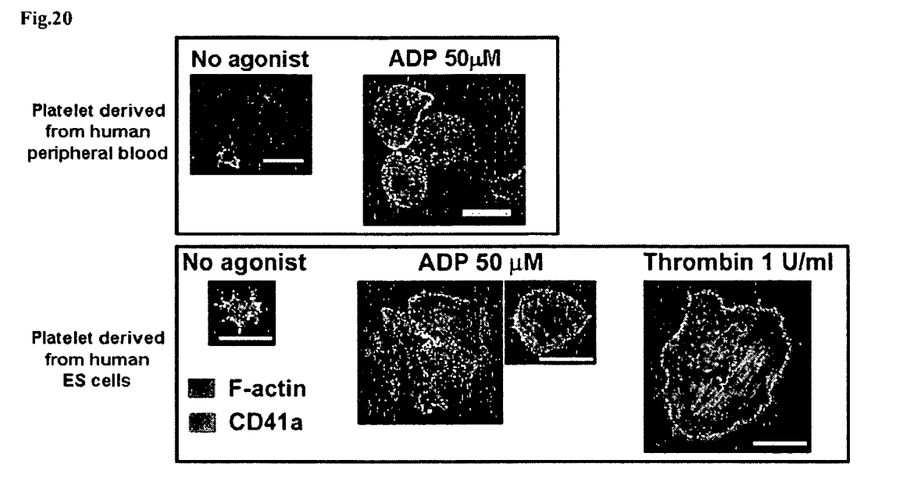
FIG. 20 shows fluorescence microscopic observation results of cytoskeletal changes exhibited by KhES-3 cell-derived platelets through ADP or thrombin stimulation, as with peripheral blood-derived platelets. For comparison, images of those exhibited by human peripheral platelets are shown thereabove. These images were obtained by staining with anti-F-actin antibodies and anti-CD41a antibodies.

These platelets were spread on a fibrinogen-immobilized slide glass through PMA stimulation (FIG. 19) and ADP or thrombin stimulation (FIG. 20), while forming actin stress fiber, one of cytoskeletal changes. The actin stress fiber that occurs after platelet activation is essential for in-vivo stable and sustained thrombus formation.

Thus, the human ES cell-derived platelets induced skeletal changes involving actin repolymerization via integrin, as with peripheral blood-derived platelets.

INDUSTRIAL APPLICABILITY

A sac-like structure of the present invention can permit efficient in-vitro amplification of blood cells and therefore brings about exceedingly beneficial effects on fields such as medical care. Particularly, the sac-like structure of the present invention has a great deal of potential as means for stably supplying platelets or the like, which cannot be prepared in vitro.

The invention claimed is:

1. A method for producing a sac-like structure enclosing hematopoietic progenitor cells, the method comprising:
   plating ES cells onto OP9 cells or 10T1/2 cells; and then
   culturing the ES cells under conditions suitable for inducing differentiation of hematopoietic progenitor cells, wherein during said culturing a culture solution is replaced without replating through day 13 following said plating, thereby forming a sac-like structure enclosing said hematopoietic progenitor cells, wherein the sac-like structure takes a follicular structure and has septa composed of UEA-1 lectin positive cells.

2. The method according to claim 1, wherein the conditions suitable for inducing differentiation of hematopoietic progenitor cells are culturing the ES cells for 14 to 16 days in the presence of VEGF.

3. The method according to claim 1, wherein the ES cells are human-derived.

4. The method according to claim 2, wherein the ES cells are human-derived.

5. A method for producing blood cells, the method comprising:
  plating ES cells onto OP9 cells or 10T1/2 cells; and then
  culturing the ES cells under conditions suitable for inducing differentiation of hematopoietic progenitor cells, wherein during said culturing a culture solution is replaced without replating through day 13 following said plating, thereby forming a sac-like structure enclosing said hematopoietic progenitor cells, wherein the sac-like structure takes a follicular structure and has septa composed of UEA-1 lectin positive cells;
  separating cells forming the septum of the sac-like structure from said hematopoietic progenitor cells;
  plating the separated hematopoietic progenitor cells onto feeder cells; and
  culturing the plated hematopoietic progenitor cells under conditions suitable for inducing differentiation of blood cells, wherein said conditions suitable for inducing differentiation of blood cells include adding at least one of the following: TPO, IL-1α, IL-3, IL-4, IL-5, IL-6, IL-9, IL-11, EPO, GM-CSF, SCF, G-CSF, Flt3 ligand and heparin to produce a type of the blood cells of interest.

6. The method according to claim 5, wherein the conditions suitable for inducing differentiation of said hematopoietic progenitor cells include culturing the ES cells for 14 to 16 days in the presence of VEGF.

7. The method according to claim 5, wherein the ES cells are human-derived.

8. The method according to claim 5, wherein the separated hematopoietic progenitor cells are plated onto 10T1/2 cells or OP9 cells as said feeder cells.

9. The method according to claim 5, wherein the blood cells are megakaryocytes and platelets.

10. The method according to claim 9, wherein the conditions suitable for inducing differentiation of blood cells include culturing the hematopoietic progenitor cells for 7 to 9 days in the presence of TPO.

11. The method according to claim 9, wherein the conditions suitable for inducing differentiation of blood cells include culturing the hematopoietic progenitor cells for 7 to 9 days in the presence of TPO, SCF, and heparin.

12. The method according to claim 1, wherein the sac-like structure has septa composed of Flk-1 positive cells.

13. A method for producing blood cells, the method comprising:
  plating ES cells onto OP9 cells or 10T1/2 cells; and then
  culturing the ES cells under conditions suitable for inducing differentiation of hematopoietic progenitor cells, thereby forming a sac-like structure enclosing said hematopoietic progenitor cells, wherein the conditions suitable for inducing differentiation of hematopoietic progenitor cells include culturing the ES cells for 14 to 16 days in the presence of VEGF, wherein the sac-like structure takes a follicular structure and has septa composed of UEA-1 lectin positive cells;
  separating cells forming the septum of the sac-like structure from said hematopoietic progenitor cells;
  plating the separated hematopoietic progenitor cells onto feeder cells; and
  culturing the plated hematopoietic progenitor cells under conditions suitable for inducing differentiation of blood cells, including culturing in a presence of TPO, wherein the blood cells are megakaryocytes and platelets.

14. The method according to claim 13 wherein the conditions suitable for inducing differentiation of blood cells include culturing the hematopoietic progenitor cells for 7 to 9 days in the presence of said TPO.

* * * * *